(12) United States Patent
Nakayama et al.

(10) Patent No.: US 10,034,998 B2
(45) Date of Patent: Jul. 31, 2018

(54) CATHETER WITH A FOLDED BRAID

(71) Applicant: ASAHI INTECC CO., LTD., Nagoya-shi, Aichi (JP)

(72) Inventors: Noriyuki Nakayama, Seto (JP); Masaaki Nihonmatsu, Kasugai (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 15 days.

(21) Appl. No.: 15/386,517

(22) Filed: Dec. 21, 2016

(65) Prior Publication Data

US 2017/0368303 A1 Dec. 28, 2017

(30) Foreign Application Priority Data

Jun. 24, 2016 (JP) ................................ 2016-125660

(51) Int. Cl.
*A61M 25/00* (2006.01)

(52) U.S. Cl.
CPC ...... *A61M 25/005* (2013.01); *A61M 25/0012* (2013.01); *A61M 25/0045* (2013.01); *A61M 25/0052* (2013.01); *A61M 25/0067* (2013.01)

(58) Field of Classification Search
CPC ............ A61M 25/005; A61M 25/0045; A61M 25/0012; A61M 25/0052; A61M 25/0053; A61M 25/0054; A61M 25/0067; A61M 2025/09066; A61M 2025/09083; A61M 2025/09091; A61M 2025/09175; A61M 2025/0915; A61M 2025/09191; A61M 25/008; A61M 25/09

See application file for complete search history.

(56) References Cited

U.S. PATENT DOCUMENTS 3,416,531 A * 12/1968 Edwards ........... A61M 25/0108
138/123
3,965,909 A * 6/1976 Waddell ................ A61L 29/146
604/269

(Continued)

FOREIGN PATENT DOCUMENTS

EP 2 695 635 A1 2/2014
EP 2 762 187 A1 8/2014

(Continued)

OTHER PUBLICATIONS

Sep. 18, 2017 Extended European Search Report issued in European Patent Application No. 17157148.2.

*Primary Examiner* — Emily Schmidt
*Assistant Examiner* — Nicholas Chidiac
(74) *Attorney, Agent, or Firm* — Oliff PLC (57) ABSTRACT

A catheter that does not require a fixing tool for fixing an end of a reinforcing body to an inner layer and does not require a separate marker to allow a user of the catheter to visually recognize a position of the catheter during procedures. The catheter includes a catheter main body having an inner layer that is a hollow tubular body, a braid that covers an outer periphery of the inner layer from a proximal end of the inner layer to a distal end of the inner layer, and an outer layer that covers an outer periphery of the braid. At least one end portion of the braid is folded under itself to form a folded part, and an end of the braid is in contact with the inner layer and is arranged in a lowest layer of the folded part.

11 Claims, 6 Drawing Sheets

(56) References Cited

U.S. PATENT DOCUMENTS

| | | | | |
|---|---|---|---|---|
| 4,516,972 | A * | 5/1985 | Samson | A61M 25/0012 |
| | | | | 138/130 |
| 4,763,647 | A * | 8/1988 | Gambale | A61M 25/09033 |
| | | | | 600/434 |
| 5,454,795 | A * | 10/1995 | Samson | A61L 29/041 |
| | | | | 600/435 |
| 5,951,539 | A * | 9/1999 | Nita | A61M 25/0053 |
| | | | | 604/524 |
| 6,508,804 | B2 | 1/2003 | Sarge et al. | |
| 7,833,218 | B2 * | 11/2010 | Lunn | A61M 25/0012 |
| | | | | 604/526 |
| 2001/0051790 | A1 | 12/2001 | Parker | |
| 2004/0167442 | A1 * | 8/2004 | Shireman | A61M 25/09 |
| | | | | 600/585 |
| 2005/0049575 | A1 * | 3/2005 | Snell | A61M 25/0017 |
| | | | | 604/544 |
| 2013/0018318 | A1 * | 1/2013 | Ravichandran | A61M 25/0012 |
| | | | | 604/172 |
| 2016/0000443 | A1 * | 1/2016 | Lilburn | A61B 17/122 |
| | | | | 606/158 |
| 2016/0339207 | A1 * | 11/2016 | Beeckler | A61B 18/1492 |
| 2017/0079546 | A1 * | 3/2017 | Costello | A61B 5/06 |

FOREIGN PATENT DOCUMENTS

| | | |
|---|---|---|
| EP | 2 923 724 A2 | 9/2015 |
| WO | 00/35527 A2 | 6/2000 |

\* cited by examiner

CATHETER WITH A FOLDED BRAID

CROSS REFERENCE TO RELATED APPLICATION

This application claims priority to Japanese Application No. 2016-125660 filed on Jun. 24, 2016, the contents of which are incorporated by reference herein in their entirety.

BACKGROUND

The disclosed embodiments relate to a medical device. Specifically, the disclosed embodiments relate to a catheter that is inserted into a body lumen such as a blood vessel or a urinary duct.

A catheter generally includes an inner layer that is a long hollow tubular body, a reinforcing body that covers an outer periphery of the inner layer, and an outer layer that covers an outer periphery of the reinforcing body.

For example, U.S. Pat. No. 6,508,804 describes a catheter including an inner layer (inner tubular member), a reinforcing body (formed by at least one filament) covering the outer periphery of the inner layer, and an outer layer covering the outer periphery of the reinforcing body. The reinforcing body is folded back on the outer periphery of the inner layer to form double layers and triple layers in the reinforcing body (see, e.g., FIG. 2 to FIG. 6).

In U.S. Pat. No. 6,508,804, the end of the reinforcing body is held between the inner layer and a radiopaque ring (see column 8, lines 26-31). The radiopaque ring is used so that a user of the catheter can visually recognize a position of the catheter during procedures; that is, the radiopaque ring functions as a so-called marker.

In the catheter described in U.S. Pat. No. 6,508,804, the reinforcing body is folded back on the outer periphery of the inner layer in the middle part of the catheter to form a plurality of layers. However, if the folded part is moved to an end of the reinforcing body, the reinforcing body is loosened. Therefore, when the folded part of the reinforcing body is moved to an end of the reinforcing body, it is necessary to fix the end of the reinforcing body to the inner layer with a fixing tool such as a ring, as described in U.S. Pat. No. 6,508,804.

Moreover, the catheter described in U.S. Pat. No. 6,508,804 separately requires a separate radiopaque ring as a marker so that a user of the catheter can visually recognize a position of the catheter during procedures.

SUMMARY

In view of the above-described problems, the disclosed embodiments provide a catheter that does not require a fixing tool for fixing an end of a reinforcing body to an inner layer, and that does not require a separate marker to allow a user of the catheter to visually recognize a position of the catheter during procedures.

In order to achieve the above-described object, the catheter includes a catheter main body having an inner layer that is a long hollow tubular body, a braid (a braided tube) that covers an outer periphery of the inner layer in a meshed form from one end of the inner layer to the other end, and an outer layer that covers an outer periphery of the braid. At least one end portion of the braid includes a folded part in which the braid is folded back (folded under itself), and an end of the braid is in contact with the inner layer and is arranged in a lowest layer (first layer) of the folded part. Thus, the braid can be fixed to the inner layer without requiring a fixing tool for fixing the end of the braid to the inner layer. For example, the end of the braid may be fixed to the inner layer in an operation performed by a so-called braider, which facilitates fixing the end of the braid.

The end of the braid may be positioned at an end of the folded part, or may be positioned in an area other than either end of the folded part. When the end of the braid is positioned in an area other than either end of the folded part, the end of the braid does not project beyond the end of the folded part and therefore does not contact or otherwise interfere with the surface of the outer layer.

The catheter may include a distal end tip connected to a distal end of the catheter main body, and the inner layer and the folded part of the braid may extend to the distal end tip. Thus, the braid can be fixed to the inner layer without requiring a fixing tool for fixing the end of the braid.

The catheter may be formed of a metal material. Thus, the folded part of the braid may function as a marker for visually recognizing a position of the catheter. Therefore, it is not necessary to provide a separate marker in the conventional manner.

DETAILED DESCRIPTION OF EMBODIMENTS

The following will describe embodiments of the present invention with reference to the drawings. In each of the drawings, the left side corresponds to a distal end of the catheter to be inserted into a body, and the right side corresponds to a proximal end of the catheter to be operated by a technician such as a physician. Note that in each drawing, proportions are exaggerated to facilitate understanding, and illustrated size does not necessarily reflect actual size.

Figure 1:
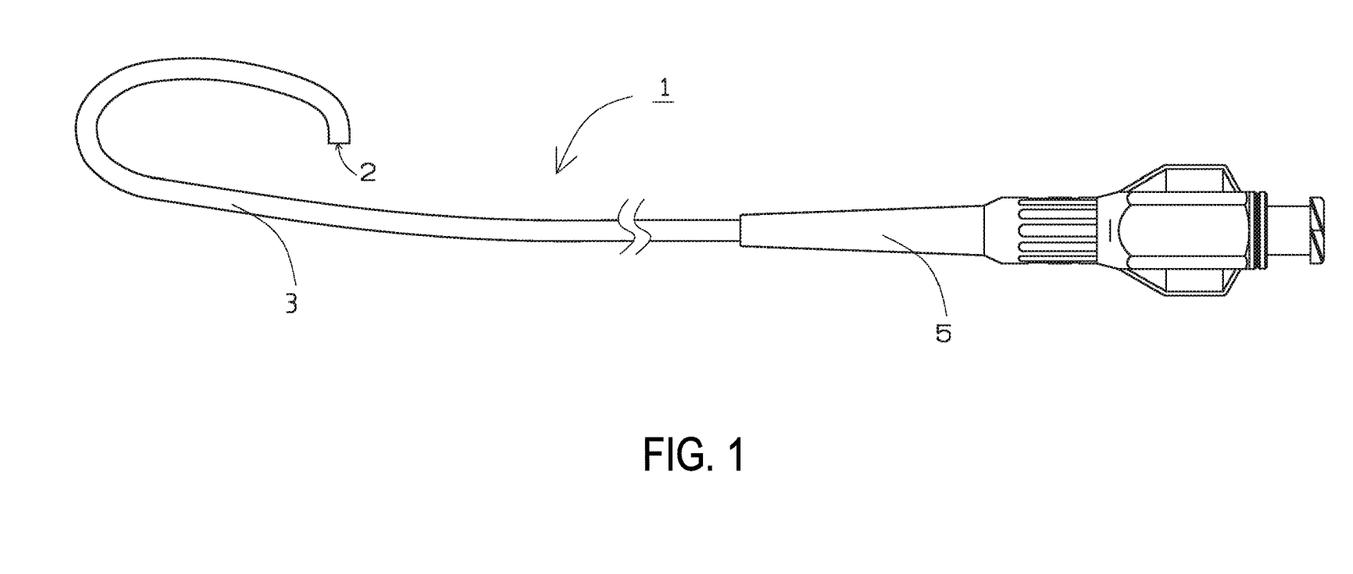
FIG. 1 is a schematic side view of a catheter according to the disclosed embodiments.
Figure 2:
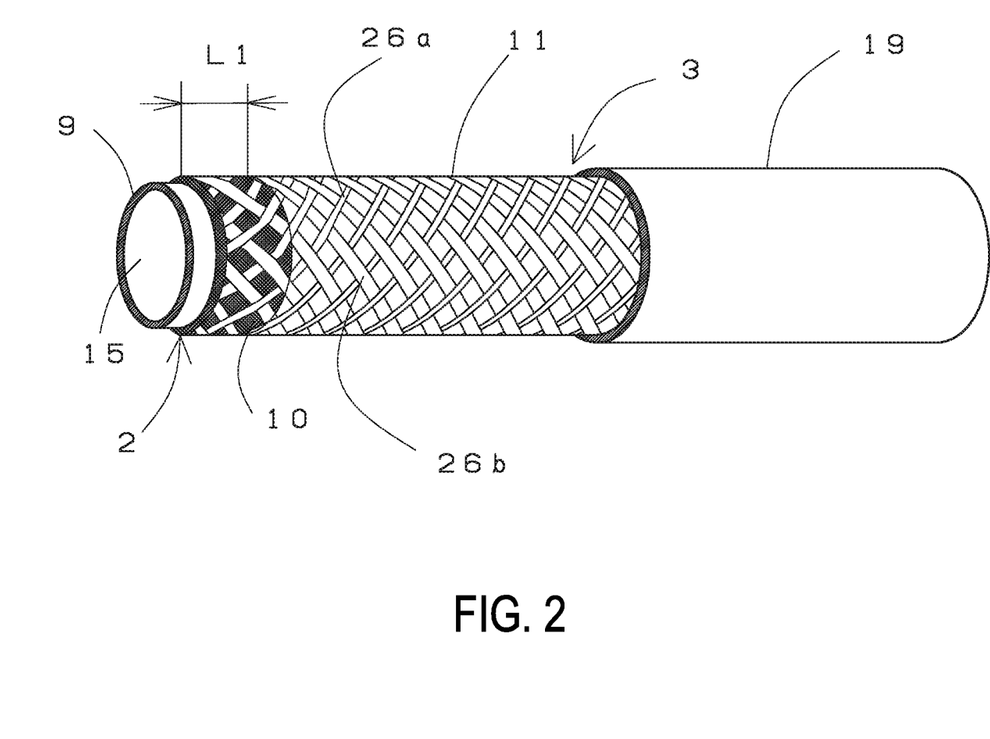
FIG. 2 shows an internal structure of a distal end of the catheter shown in FIG. 1.
Figure 3:
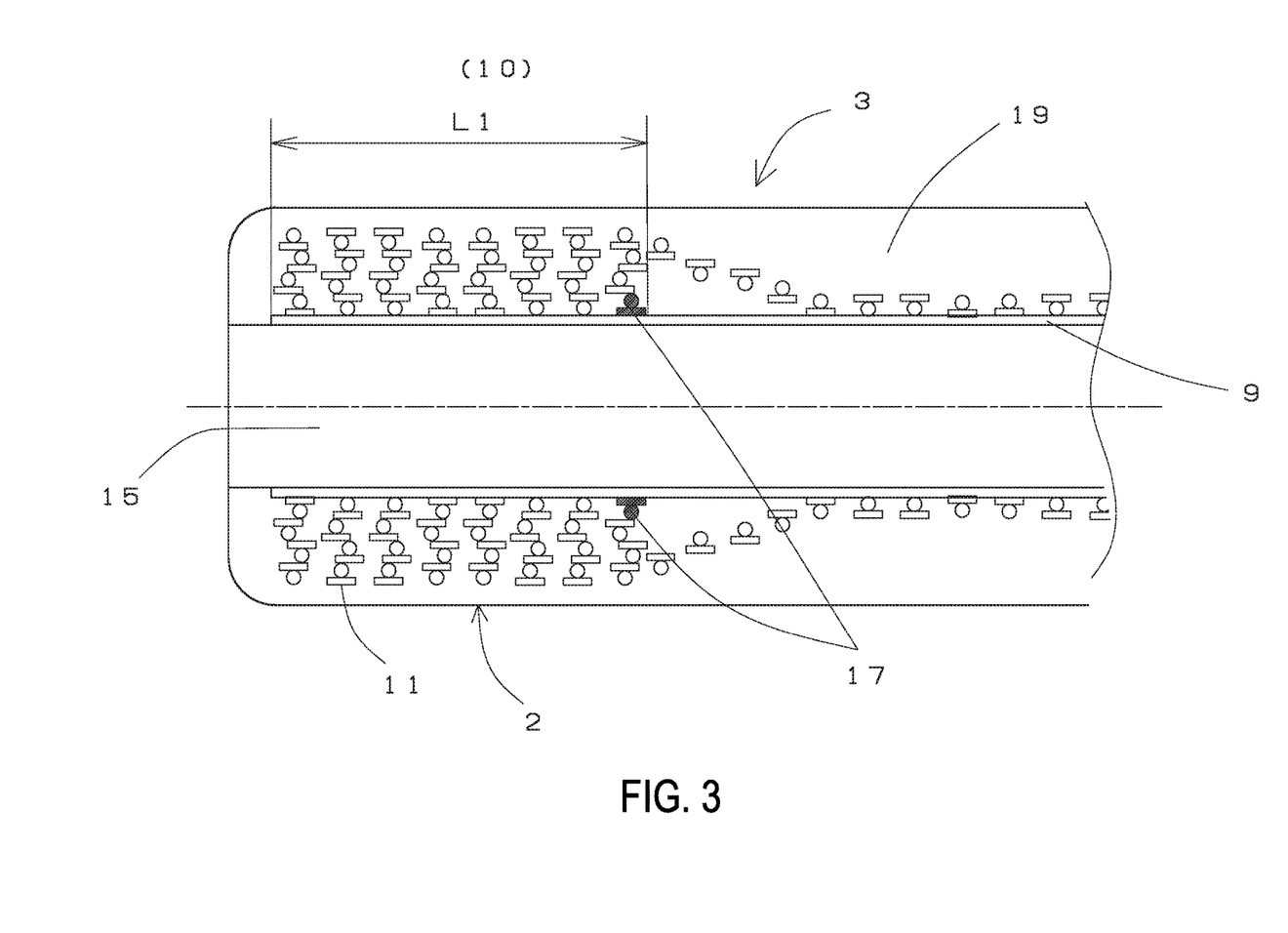
FIG. 3 is a cross-sectional view of the distal end of the catheter shown in FIGS. 1 and 2.

FIG. 1 is a schematic side view of a catheter according to the disclosed embodiments. FIG. 2 shows an internal structure of a distal end of the catheter shown in FIG. 1. FIG. 3 is a cross-sectional view of the distal end of the catheter shown in FIGS. 1 and 2.

In FIG. 1, a catheter 1 is a tubular medical instrument with an entire length of, for example, 1200 mm. The catheter 1 includes a flexible catheter main body 3 and a connector 5 connected to a proximal end of the catheter main body 3.

As illustrated in FIG. 2, the catheter main body 3 has a three-layer structure including an inner layer 9 positioned on an inner side of the catheter main body 3 in a radial direction, a mesh formed braid 11 (a braided tube) covering an outer periphery of the inner layer 9, and an outer layer 19 covering an outer periphery of the braid 11.

The inner layer 9 is a long hollow tubular body formed of resin, and has therein a lumen 15 for inserting a guide wire or other catheters. The resin material forming the inner layer 9 is not particularly limited. For example, polytetrafluoroethylene (PTFE) may be used.

The braid 11 shown in FIG. 1 is formed of 16 pieces in total of element wire, including 8 pieces of first element wire 26a and 8 pieces of second element wire 26b that are alternately braided in a meshed form (i.e., in an "8×8" configuration). In the catheter 1, 8 pieces of first element wire 26a are wound in a counterclockwise direction toward the distal end of the catheter 1, and 8 pieces of second element wire 26b are wound in a clockwise direction toward the distal end of the catheter 1, as illustrated in FIG. 2.

The configuration of the element wires forming the braid 11 is not limited to 8 pieces×8 pieces. For example, the configuration may be symmetrical with 4 pieces×4 pieces, 2 pieces×2 pieces or the like, or asymmetrical with 4 pieces×8 pieces, 2 pieces×4 pieces or the like.

Moreover, an element wire width of the first element wire 26a and an element wire width of the second element wire 26b may be the same, or one of the element wire widths may be larger than the other.

The braid 11 may be formed, as shown in FIGS. 2 and 3, by alternately braiding the first element wire 26a and the second element wire 26b two by two. However, the disclosed embodiments are not limited thereto, and the braid 11 may be formed by alternately braiding element wires one by one, for example.

The first element wire 26a and the second element wire 26b may be formed of stainless steel (SUS304 or SUS316). However, a metal other than stainless steel (e.g., platinum, tungsten, or the like) or a material other than metal (e.g., reinforced plastic) may be used. Moreover, the material of the first element wire 26a and the second element wire 26b may be the same or different.

When the first element wire 26a and/or the second element wire 26b are formed of metal, they can function as a marker for visually recognizing a position of the catheter, as described later. Thus, it is not necessary to provide a separate marker.

In the catheter 1 as shown in FIG. 3, the first element wire 26a is a round wire with a round cross section and the second element wire 26b is a so-called flat wire with a rectangular cross section. However, element wires may have other cross-sectional shapes; e.g., the first element wire 26a and the second element wire 26b may both be round wires having a round cross section, or may both be flat wires having a rectangular cross section.

The braid 11 covers the outer periphery of the inner layer 9 proximal to the distal end portion 2, and is folded back (folded under itself) at a distal end portion 2 to form a folded part 10 with a length L1, as illustrated in FIG. 2 and FIG. 3. Moreover, an end 17 of the braid 11 is in contact with the inner layer 9, and is arranged in a lowest layer of the folded part 10 at a proximal end of the folded part 10. The number of times the braid 11 is folded in the folded part 10 is not particularly limited as long as it is an even number. In the catheter 1 as shown in FIG. 3, the braid 11 is folded four times.

The folded part 10 may be formed by first bringing the end 17 of the braid 11 into contact with the inner layer 9 at a proximal end of the distal end portion 2 and braiding the first layer of the folded part 10 toward a distal end of the distal end portion 2, and then folding the braid 11 back at the distal end of the distal end portion 2 to braid the second layer of the folded part 10 toward the proximal end of the distal end portion 2. Thereafter, the braid 11 is folded back at the proximal end of the distal end portion 2 to braid the third layer of the folded part 10 toward the distal end of the distal end portion 2. Finally, the braid 11 is folded back again at the distal end of the distal end portion 2 to braid the fourth layer of the folded part 10 toward the proximal end of the distal end portion 2 to complete the folded part 10. Subsequently, the braid 11 is braided toward the proximal end of the catheter 1 to cover the inner layer 9.

Note that the end 17 of the braid 11 is positioned at the proximal end of the folded part 10. However, the end 17 may be positioned at the distal end of the folded part 10. In this case, the braid 11 is folded an odd number of times (e.g., three times).

The outer layer 19 is formed of resin, and covers the inner layer 9 and the braid 11. The resin material forming the outer layer 19 is not particularly limited, and polyamide, polyamide elastomer, polyester, polyurethane, and the like can be used. For example, in the outer layer 19, polyamide is used.

The proximal end of the catheter main body 3, the proximal end of the inner layer 9, the proximal end of the braid 11, and the proximal end of the outer layer 19 are firmly fixed by the connector 5.

The catheter 1 includes the catheter main body 3 having the inner layer 9 that is a long hollow tubular body, the braid 11 that covers the outer periphery of the inner layer 9 in a meshed form from the distal end of inner layer 9 to the proximal end of the inner layer 9, and the outer layer 19 covering the outer periphery of the braid 11. The braid 11 is folded back at the distal end portion 2, and the end 17 of the braid 11 is in contact with the inner layer 9 and is arranged in a lowest layer of the folded part 10. Thus, the braid 11 can be fixed to the inner layer 9 without requiring a fixing tool for fixing the end 17 of the braid 11 to the inner layer 9.

In the catheter 1, the end 17 of the braid 11 is applied to the inner layer 9 ("fixed") in an operation performed by a so-called braider, which facilitates fixing the end 17 of the braid 11 to the inner layer 9.

Moreover, even when the braid 11 of the catheter 1 is formed of low-cost stainless steel (SUS304 or SUS316), the folded part 10 can function as a marker for visually recognizing a position of the catheter. Therefore, it is not necessary to provide a separate marker in the conventional manner.

The inventors studied the effect of folding stainless steel braids (SUS304 and SUS316) on visibility. In particular, the inventors studied the visibility of braids folded two to four times. Visibility was improved when the number of folds was increased from two to three times, and was further improved when the number of folds was increased from three to four times. However, even when the braid included only two folds, the position of the catheter could be recognized visually, and the folded part could function as a marker.

In the catheter 1, the folded part 10 of the braid 11 is provided at the distal end portion 2 of the catheter main body 3. However, the folded part 10 may be provided at a proximal end portion of the catheter main body 3. Also in such a case, the end 17 of the braid 11 may be provided at the distal end or the proximal end of the folded part 10.

Figure 4:
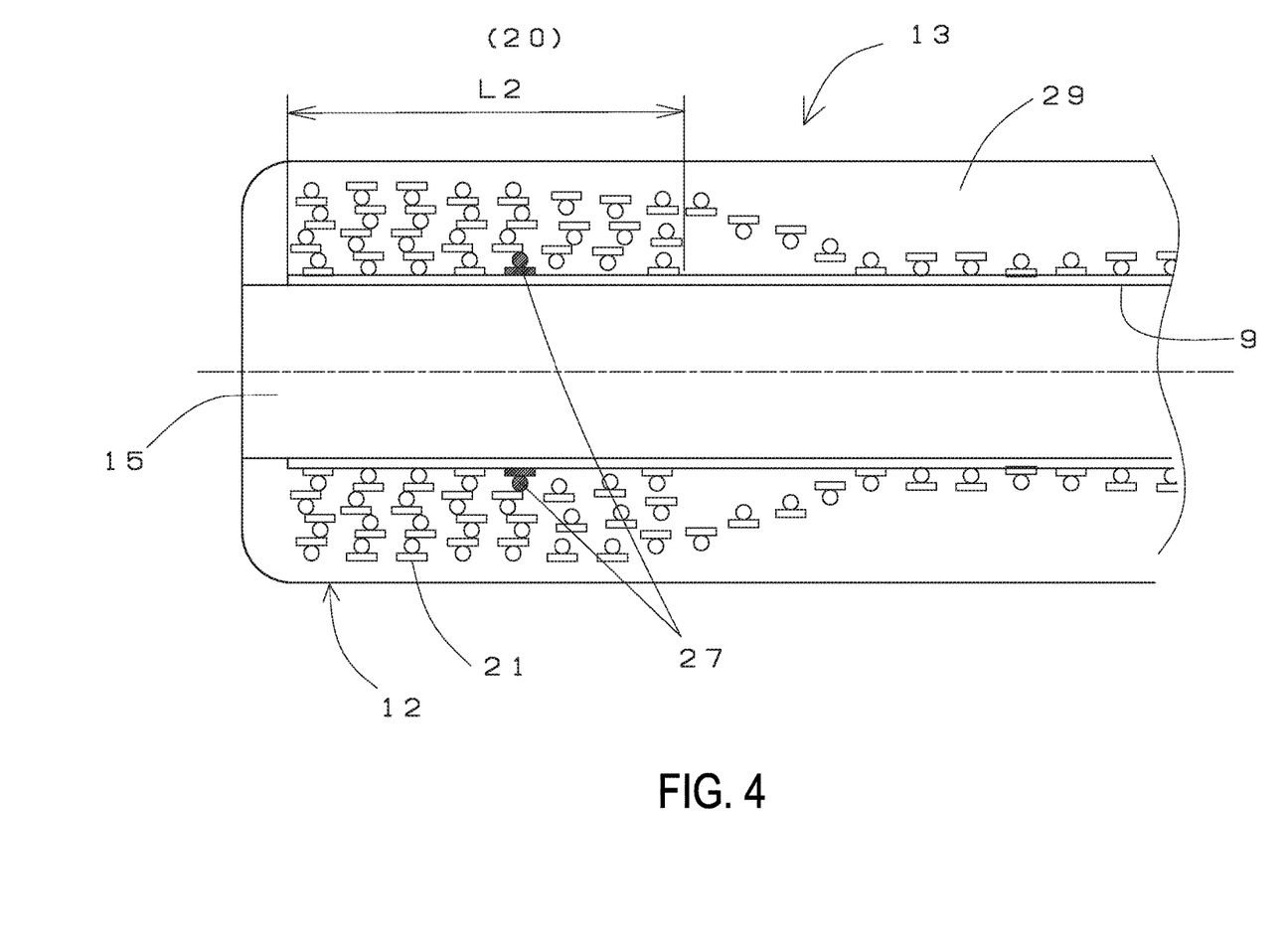
FIG. 4 is a cross-sectional view of a distal end of a catheter according to the disclosed embodiments.

In FIG. 4, a catheter main body 13 has a three-layer structure including the inner layer 9 positioned on an inner side of the catheter main body 13 in a radial direction, a mesh formed braid 21 covering the outer periphery of the inner layer 9, and an outer layer 29 covering an outer periphery of the braid 21.

The braid 21 covers the outer periphery of the inner layer 9 proximal to a distal end portion 12 of the catheter, and is folded back at the distal end portion 12 to form a folded portion 20 with a length L2, as illustrated in FIG. 4.

Moreover, an end 27 of the braid 21 is in contact with the inner layer 9, and is arranged in a lowest layer in a middle position (middle portion) of the folded part 20.

Similarly to the braid 11, the braid 21 is formed of 16 (8×8) pieces in total of element wire including 8 pieces of first element wire 26a and 8 pieces of second element wire 26b that are alternately braided in a meshed form. The 8 pieces of first element wire 26a are wound in a counter-clockwise direction toward a distal end of the braid 21, and the 8 pieces of second element wire 26b are wound in a clockwise direction toward the distal end of the braid 21.

The configuration of element wires forming the braid 21 is not limited to 8 pieces×8 pieces. For example, the configuration may be symmetrical with 4 pieces×4 pieces, 2 pieces×2 pieces or the like, or asymmetrical with 4 pieces×8 pieces, 2 pieces×4 pieces or the like.

Moreover, an element wire width of the first element wire 26a and an element wire width of the second element wire 26b may be the same, or one of the element wire widths may be larger than the other.

The braid 21 may be formed, as shown in FIG. 4, by alternately braiding the first element wire 26a and the second element wire 26b two by two. However, the embodiment is not limited thereto, and the braid 21 may be formed by alternately braiding element wires one by one, for example.

The first element wire 26a and the second element wire 26b may be formed of stainless steel (SUS304 or SUS316). However, a metal other than stainless steel (e.g., platinum, tungsten, or the like) or a material other than metal (e.g., reinforced plastic) may be used. Moreover, the material of the first element wire 26a and the second element wire 26b may be the same or different.

When the first element wire 26a and/or the second element wire 26b are formed of metal, they can function as a marker for visually recognizing a position of the catheter. Thus, it is not necessary to provide a separate marker.

In the braid 21, the first element wire 26a is a round wire with a round cross section and the second element wire 26b is a so-called flat wire with a rectangular cross section. However, the element wires may have other cross-sectional shapes; e.g., the first element wire 26a and the second element wire 26b may both be round wires having a round cross section, or may both be flat wires having a rectangular cross section.

The number of times the braid 21 is folded in the folded part 20 is not particularly limited as long as it is an even number. In FIG. 4, the braid 21 is folded four times.

The folded part 20 may be formed by first bringing the end 27 of the braid 21 into contact with the inner layer 9 at a middle position of the distal end portion 12 and braiding the first layer of the folded part 20 toward a distal end of the distal end portion 12, and then folding the braid 21 back at the distal end of the distal end portion 12 to braid the second layer of the folded part 20 toward a proximal end of the distal end portion 12. Thereafter, the braid 21 is folded back at the proximal end of the distal end portion 12 to braid the third layer of the folded part 20 toward the distal end of the distal end portion 12. Finally, the braid 21 is folded back again at the distal end of the distal end portion 12 to braid the fourth layer of the folded part 20 toward the proximal end of the distal end portion 12, and the formation of the folded part 20 is finished. Subsequently, the braid 21 is braided toward the proximal end of the inner layer 9 to cover the inner layer 9.

Note that the braid 21 is braided from the end 27 toward the distal end of the distal end portion 12. That is, the lowest layer of the folded part 20 extends from the middle position of the folded part 20 to the distal end of the folded part 20. However, the braid 21 may be braided from the end 27 toward the proximal end of the folded part 20 so that the lowest layer of the folded part 20 extends from the middle position of the folded part 20 to the proximal end of the folded part 20. In this case, the number of folds in the folded part 20 is an odd number (e.g., three folds).

The outer layer 29 is formed of resin, and covers the inner layer 9 and the braid 21. The resin material forming the outer layer 29 is not particularly limited, and polyamide, polyamide elastomer, polyester, polyurethane, and the like can be used. For example, in the outer layer 29, polyurethane is used.

In FIG. 4, the end 27 of the braid 21 is in a middle position of the folded part 20. Thus, the end 27 of the braid 21 does not project beyond the end of the folded part 20 and does not have any influence on the surface of the outer layer 29.

Moreover, even when the braid 21 is formed of low-cost stainless steel (SUS304 or SUS316), the folded part 20 can function as a marker for visually recognizing a position of the catheter. Therefore, it is not necessary to provide a separate marker in the conventional manner.

Note that the end 27 of the braid 21 in FIG. 4 is arranged in a middle position of the folded part 20. However, the disclosed embodiments are not limited thereto, and the same effects can be obtained as long as the end 27 of the braid 21 is arranged in an area other than at either end of the folded part 20.

Figure 5:
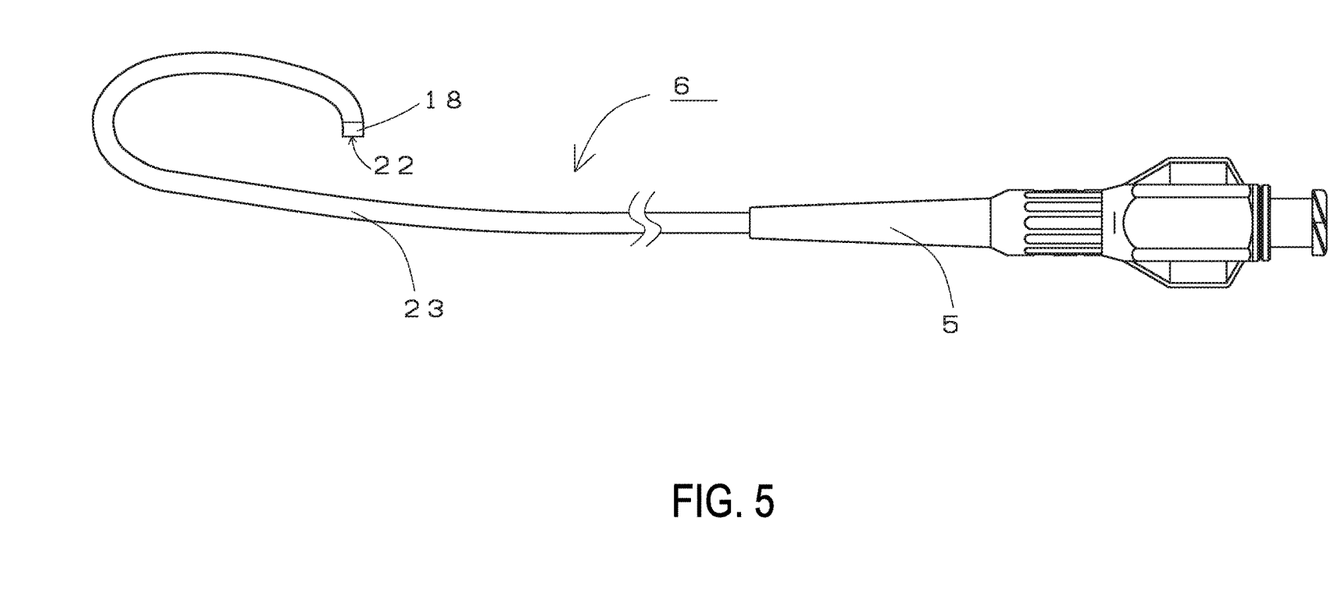
FIG. 5 is a schematic side view of a catheter according to the disclosed embodiments.
Figure 6:
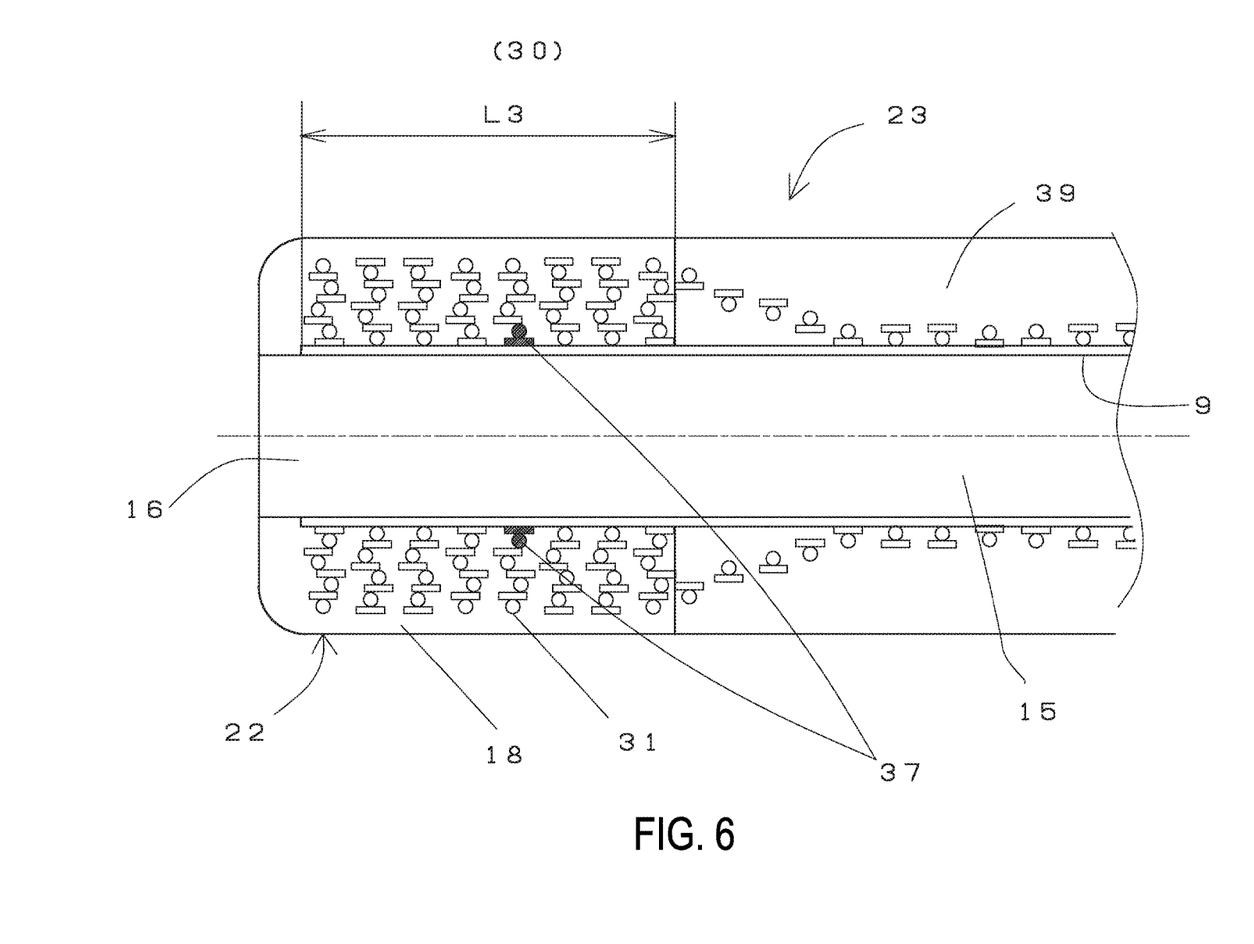
FIG. 6 is a cross-sectional view of a distal end of the catheter shown in FIG. 5.

FIG. 5 is a schematic side view of a catheter according to the disclosed embodiments. FIG. 6 is a cross-sectional view of a distal end of the catheter shown in FIG. 5.

In FIG. 5, a catheter 6 is a tubular medical instrument with an entire length of, for example, 1200 mm. The catheter 6 includes a distal end portion 22, a flexible catheter main body 23, a distal end tip 18 connected to a distal end of the catheter main body 23, and the connector 5. At a proximal end of the catheter main body 23, the proximal end of the inner layer 9, a proximal end of the braid 31, and a proximal end of the outer layer 39 are firmly fixed by the connector 5.

The distal end tip 18 is a cylindrical member having an opening 16 communicating with the lumen 15. The resin forming the distal end tip 18 is not particularly limited, and polyurethane, polyurethane elastomer, or the like may be used.

The distal end tip 18 may contain radiopaque powder. For example, when the distal end tip 18 contains radiopaque powder (e.g., tungsten powder) in a range of about 65 wt % to about 90 wt %, a technician such as a physician can accurately visualize and control a position of the catheter in coronary angiography.

The catheter main body 23 has a three-layer structure including the inner layer 9 positioned on an inner side of the catheter main body 23 in a radial direction, a mesh formed braid 31 covering an outer periphery of the inner layer 9, and an outer layer 39 covering an outer periphery of the braid 31, as illustrated in FIG. 6.

The braid 31 covers the outer periphery of the inner layer 9 proximal to a distal end portion 22, and is folded back at the distal end portion 22 to form a folded portion 30 with a length L3, as illustrated in FIG. 6. Moreover, an end 37 of the braid 31 is in contact with the inner layer 9, and is arranged in a lowest layer in a middle position of the folded part 30.

Similarly to the braid 11, the braid 31 is formed of 16 (8×8) pieces in total of element wire including 8 pieces of first element wire 26a and 8 pieces of second element wire 26b that are alternately braided in a meshed form. The 8 pieces of first element wire 26a are wound in a counterclockwise direction toward a distal end of the braid 31, and the 8 pieces of second element wire 26b are wound in a clockwise direction toward the distal end of the braid 31.

The configuration of element wires forming the braid 31 is not limited to 8 pieces×8 pieces in the embodiment. For example, the configuration may be symmetrical with 4 pieces×4 pieces, 2 pieces×2 pieces or the like, or asymmetrical with 4 pieces×8 pieces, 2 pieces×4 pieces or the like.

Moreover, an element wire width of the first element wire 26a and an element wire width of the second element wire 26b may be the same, or one of the element wire widths may be larger than the other.

The braid 31 may be formed, as shown in FIG. 6, by alternately braiding the first element wire 26a and the second element wire 26b two by two. However, the embodiment is not limited thereto, and the braid 31 may be formed by alternately braiding element wires one by one, for example.

The first element wire 26a and the second element wire 26b may be formed of stainless steel (SUS304 or SUS316). However, a metal other than stainless steel (e.g., platinum, tungsten, or the like) or a material other than metal (e.g., reinforced plastic) may be used. Moreover, the material of the first element wire 26a and the second element wire 26b may be the same or different.

When the first element wire 26a and/or the second element wire 26b are formed of metal, they can function as a marker for visually recognizing a position of the catheter. Thus, it is not necessary to provide a separate marker.

In the braid 31, the first element wire 26a is a round wire with a round cross section and the second element wire 26b is a so-called flat wire with a rectangular cross section. However, the element wires may have other cross-sectional shapes; e.g., the first element wire 26a and the second element wire 26b may both be round wires having a round cross-sectional shape or may both be flat wires having a rectangular cross-sectional shape.

The number of times the braid 31 is folded in the folded part 30 is not particularly limited as long as it is an even number. In FIG. 6, the number braid 31 is folded four times.

The folded part 30 may be formed by first bringing the end 37 of the braid 31 into contact with the inner layer 9 at a middle position of the distal end portion 22 and braiding the first layer of the folded part 30 toward a distal end of the distal end portion 22, and then folding the braid 31 back at the distal end of the distal end portion 22 to braid the second layer of the folded part 30 toward a proximal end of the distal end portion 22. Thereafter, the braid 31 is folded back at the proximal end of the distal end portion 22 to braid the third layer of the folded part 30 toward the distal end of the distal end portion 22. Finally, the braid 31 is folded back at the distal end of the distal end portion 22 to braid the fourth layer of the folded part 30 toward the proximal end of the distal end portion 22, and the formation of the folded part 30 is finished. Subsequently, the braid 31 is braided toward the proximal end of the inner layer 9 to cover the inner layer 9.

Note that the braid 31 is braided from the end 37 toward the distal end of the distal end portion 22. However, it may be braided from the end 37 toward the proximal end of the distal end portion 22. In this case, the number of folds in the folded part 30 is an odd number (e.g., three folds).

The outer layer 39 is formed of resin, and covers the inner layer 9 and the braid 31. The resin material forming the outer layer 39 is not particularly limited, and polyamide, polyamide elastomer, polyester, polyurethane, and the like can be used. For example, in the outer layer 39, polyurethane is used.

In the catheter 6, the distal end tip 18 is connected to a distal end of the catheter main body 23, and the inner layer 9 and the folded part 30 of the braid 31 extend to the distal end tip 18. Thus, the braid 31 can be fixed to the inner layer 9 without requiring a fixing tool for fixing the end 37 of the braid 31.

In the catheter 6, the end 37 of the braid 31 is arranged in a middle position of the folded part 30. Thus, the end 37 of the braid 31 does not project beyond the end of the folded part 30 and does not have any influence on the surface of the outer layer 39.

Moreover, even when the braid 31 of the catheter 6 is formed of low-cost stainless steel (SUS304 or SUS316), the folded part 30 can function as a marker for visually recognizing a position of the catheter 6. Therefore, it is not necessary to provide a separate marker in the conventional manner.

Note that the end 37 of the braid 31 in FIG. 6 is arranged in a middle position of the folded part 30. However, the disclosed embodiments are not limited thereto, and the same effect can be obtained as long as the end 37 of the braid 31 is arranged in an area other than either end of the folded part 30.

What is claimed is:

1. A catheter comprising:
   a catheter main body including:
      an inner layer that is a hollow tubular body,
      a braid that covers an outer periphery of the inner layer from a proximal end of the inner layer to a distal end of the inner layer, and
      an outer layer that covers an outer periphery of the braid,
   wherein:
      a distal end portion of the braid is folded under itself multiple times to form a folded part comprising multiple folds, and at least one of the multiple folds is at a distal end of the folded part,
      the distal end of the folded part is positioned at the distal end of the inner layer, and a proximal end of the folded part is positioned distal to the proximal end of the inner layer, and
      an end of the braid is in contact with the inner layer and is arranged in a lowest layer of the folded part.

2. The catheter according to claim 1, wherein the end of the braid is not positioned at either the distal end of the folded part or the proximal end of the folded part.

3. The catheter according to claim 2, wherein the end of the braid is positioned at a middle portion of the folded part.

4. The catheter according to claim 2, further comprising:
   a distal end tip connected to a distal end of the catheter main body,
   wherein the inner layer and the folded part of the braid extend to the distal end tip.

5. The catheter according to claim 4, wherein the braid is formed of a metal material.

6. The catheter according to claim 2, wherein the braid is formed of a metal material.

7. The catheter according to claim 1, wherein the end of the braid is positioned at either the distal end of the folded part or the proximal end of the folded part.

8. The catheter according to claim 1, further comprising:
   a distal end tip connected to a distal end of the catheter main body, wherein the inner layer and the folded part of the braid extend to the distal end tip.

9. The catheter according to claim 8, wherein the braid is formed of a metal material.

10. The catheter according to claim 1, wherein the braid is formed of a metal material.

11. The catheter according to claim 1, wherein two or more of the multiple folds are at the distal end of the folded part.

* * * * *